(12) United States Patent
Lans

(10) Patent No.: US 6,916,178 B2
(45) Date of Patent: Jul. 12, 2005

(54) DENTAL SPLINT AND SPLINTING METHOD

(75) Inventor: Maris Lans, Baltimore, MD (US)

(73) Assignee: Eastflex Corp., Indianapolis, IN (US)

( * ) Notice: Subject to any disclaimer, the term of this patent is extended or adjusted under 35 U.S.C. 154(b) by 43 days.

(21) Appl. No.: 10/369,868

(22) Filed: Feb. 21, 2003

(65) Prior Publication Data
US 2004/0166477 A1 Aug. 26, 2004

(51) Int. Cl.⁷ .............................................. A61C 13/12
(52) U.S. Cl. ........................................ 433/181; 433/215
(58) Field of Search ................................ 433/215, 181; 403/174, 294, 408.1; D8/349; 52/396; 411/531; 49/475

(56) References Cited

U.S. PATENT DOCUMENTS

| 1,211,494 | A | | 1/1917 | Shaw |
| 2,087,047 | A | | 7/1937 | Sheven |
| 2,213,963 | A | | 9/1940 | Myerson |
| 2,826,814 | A | | 3/1958 | Sappey et al. |
| 3,822,472 | A | * | 7/1974 | Garfinkel .................... 433/215 |
| 4,260,383 | A | * | 4/1981 | Weissman ................... 433/225 |
| 4,310,312 | A | | 1/1982 | Keller et al. |
| 4,380,435 | A | * | 4/1983 | Raeder et al. .............. 433/180 |
| 4,445,862 | A | | 5/1984 | Chiaramonte et al. |
| 4,735,571 | A | * | 4/1988 | Salvo ......................... 433/215 |
| 4,826,436 | A | | 5/1989 | Shoher et al. |
| 5,358,405 | A | * | 10/1994 | Imai .......................... 433/215 |
| 5,888,068 | A | | 3/1999 | Lans et al. |
| 6,050,820 | A | | 4/2000 | Lans et al. |

* cited by examiner

Primary Examiner—John J Wilson

(57) ABSTRACT

An apparatus and method are described for splinting teeth, the apparatus comprising a splint formed from a flat and relatively think rigid sheet, with two support prongs extending in opposite directions from each other and connected by an arch portion. The method is comprised of applying the splint, in aligned grooves cut into the labial or lingual surface of two adjacent teeth, each groove being large enough to accommodate the splint. The grooves are partially filled, with a flowable resin and the splint is then embedded in the composite resin in the grooves.

1 Claim, 1 Drawing Sheet

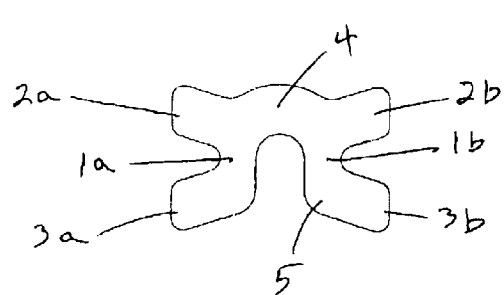
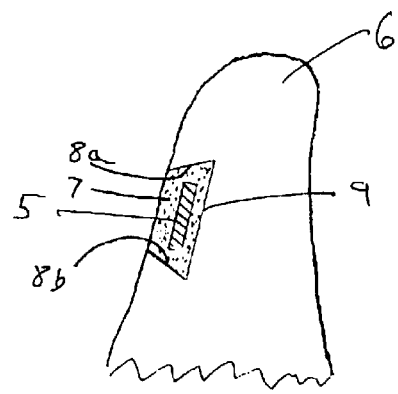
FIG.1
FIG.3
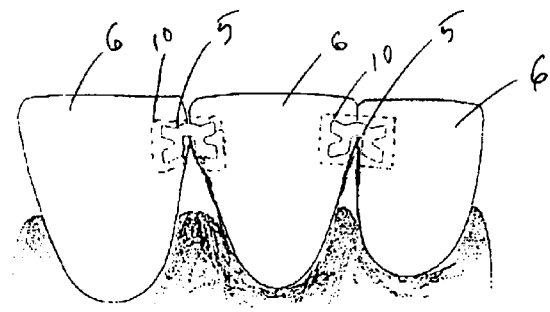
FIG.2

US 6,916,178 B2

DENTAL SPLINT AND SPLINTING METHOD

FIELD OF THE INVENTION

This invention is directed to a dental splint and method for installing it in adjacent teeth. The splint is formed of a rigid sheet material and has two support prongs extending in opposite direction to each other from two shoulders that are connected by an arch portion that extends between the shoulders. The method for installing requires that aligned grooves be cut into adjacent teeth. The grooves are partially filled with composite resin after which the splint is embedded in the composite resin, which is then cured and finished to a smooth surface.

BACKGROUND OF THE INVENTION

In the current practice of dentistry, clinicians often attempt to treat the problem of periodontally compromised teeth, ("loose teeth", that is ones not strongly supported by the gum tissue and boney structures surrounding them). The most common approach to treating this problem is the use of splints which are means to attach the teeth to one another. In this way the more stable teeth help to stabilize the looser ones and the entire row of splinted teeth is more stable.

There are several standard methods currently used by dental clinicians to effect splinting. One is by means of castings which involves expensive and time consuming custom fabricating and fitting. The castings are bonded to the lingual sides of teeth. Another similar technique employs prefabricated resin ribbons bonded to the lingual sides of teeth. Both of these aspects such as timing, pressure, blending and application are critical. These techniques are also problematic because the bond may weaken and spaces develop between the teeth and the splint. The patient is generally not aware of the spaces and they become areas prone to decay.

Another splinting technique is by wire ligature. The dental clinician cuts in the lingual side of the entire row of teeth, a narrow horizontal channel large enough to accommodate an orthodontic wire which is fitted therein and bonded in place using a composite resin. This requires considerable effort of the clinician because the cutting is continuous along the entire inner periphery of the teeth. Failure of the bond may occur at any location along the wire's channel without being apparent to the patient.

A third approach to splinting uses a spackling of composite resins (without any additional retentive devices) which is applied to the lingual surfaces of the teeth. One of the major disadvantages to this technique is that it obliterates the embrasures (space between the teeth). This makes cleaning by the patient difficult. It is also subject to the problems of other techniques which depend on bonding.

It is, accordingly, an object of the present invention to provide an improved splint and splinting method that requires minimal preparation and minimal bonding.

DISCLOSURE OF THE PRIOR ART

Some aspects of the present invention are similar to methods taught in applicant's prior

BRIEF DESCRIPTION OF THE DRAWINGS

FIG. 1 is a front elevational view of the splint.

FIG. 2 is a front elevational view illustrating the manner in which splints might be located relative to adjacent teeth.

FIG. 3 is a cross sectional side view of a partial tooth with an implanted splint.

SUMMARY OF THE INVENTION

In accordance with the present invention, a method and apparatus are provided for splinting teeth. The apparatus of the invention comprises a splint formed from a flat and relatively thin metal sheet. The splint has two support prongs extending in opposite directions to each other from two shoulders that are connected by an arch portion that extends between the upper ends of the two shoulders.

The method for applying a splint, requires that a small, flat groove be cut into each of the two adjacent teeth. The grooves are aligned and cut at the contact point of the teeth. Each groove is slightly larger than the outer circumference of the two prongs and shoulders of the splint. The sides of the grooves are undercut, so the bottom circumference of the groove is greater than the top. The grooves are lined with bonding agents and a flowable composite resin is placed in each groove. The splint is then placed in the aligned grooves so that the shoulder and prongs on one side of the splint are in one tooth, and the shoulder and prongs on the opposite side of the splint are in the adjacent teeth. The arch portion extends between and connects the adjacent teeth. The prongs and shoulders are embedded in the composite resin in the groove.

The placement of the splint will cause the composite resin to flow around the splint, and envelop it. If necessary, more composite resin may be added to completely fill the groove. The resin is then cured with a curing light of standard use. The filled groove is finished and polished to a smooth surface consistent with the tooth. The actual joint area between adjacent teeth is minimal because of the splint's structure, i.e., the prongs and shoulders are embedded into a substantial portion of the tooth giving it great strength and stability., but the arch portion is at the upper end and above the shoulders of the splint forming a narrow and flexible connection between the adjacent teeth. The embrasure areas are unencumbered allowing for access to cleaning. Each individual joint is a separate entity capable of withstanding the forces attempting to dislodge it during function because the resin/metal/resin joint that is obtained is capable of dispersing the forces laterally as in any sandwich design. Should any single joint give way, it can be readily diagnosed and repaired without affecting the other joints. Most commonly splinted teeth in the human dentition are the lower six anteriors, due to their short conical root formation. The method of the present invention requires ordinary skill on the part of the clinician. The splints of the present invention do not add any additional bulk of material to the contours of the teeth which can affect speech and make cleaning more difficult. Minimizing the resin/tooth interface also minimizes the potential for recurrent decay along the margins of the resin and tooth.

DETAILED DESCRIPTION OF THE DRAWINGS

Reference will now be made in detail to the preferred embodiment of the invention presented here and illustrated in the accompanying drawings.

FIG. 1 is the dental splint, formed from a sheet of stainless steel or titanium 0.007 inches thick. It is comprised of opposing shoulder portions 1a and 1b, out from which extend the upper support prongs 2a and 2b, and the lower support prongs 3a and 3b. Connecting the opposing shoulders 1a and 1b is arch portion 4. Collectively, the splint is identified by reference numeral 5.

FIG. 2 illustrates the position in which the splints 5 are attached to adjacent teeth 6 at the contact point between the teeth. The slots 10 are indicated by the dotted line.

FIG. 3 illustrates the method by which the splint 5 is embedded in adjacent teeth 6. Slots 10 are cut into adjacent teeth 6 at their point of contact, using a simple inverted core carbide bur. Each slot 10 has a flat bottom surface 9, an upper undercut side 8a and a lower undercut side 8b. The end wall of slot 10 (not shown in the drawings) is also undercut in a manner similar to the slot's sides 8a and 8b.

The slot 10 is lined with standard bonding agents and a flowable composite resin 7 is introduced into the slot 10 and gently forced down into the composite resin 7, causing the resin to flow around the splint 5, enveloping it. More composite resin 7 may then be added to completely fill slot 10. The composite resin 7 is then cured with such curing light as is appropriate for the specific composite resin used.

It will be appreciated that by this method a minimal joint contact between adjacent teeth 6 is established, which does not impinge on the embrasures between the teeth and does not interfere with cleaning them.

It will also be appreciated that by undercutting the sides 8a and 8b of slot 10, as well as the end wall of slot 10, the cured composite resin 7 and the enveloped splint 5 are wedged into position and cannot easily separate or be dislodged from slot 10.

It will be further appreciated that the configuration of splint 5, with its prongs 2a, 2b, 3a and 3b provide a maximal extent of surface to be engaged by the composite resin 7; and each arch portion 4 provide a minimal joint contact between the adjacent teeth.

In the preferred embodiment of this invention the slot 10 and splint 5 are substantially smaller relative to the adjacent teeth 6 than illustrated in FIG. 2 and FIG. 3. Showing them in a larger form is for the purpose of better graphic clarity.

It will be further apparent to those skilled in the art that various modifications and variations can be made in the dental splint and method of the present invention without departing from the spirit or scope of the invention. Thus, it is intended that the present invention cover the modifications and variations of this invention that come within the scope of the appended claims and their equivalents.

What is claimed is:

1. A dental splint for connecting and supporting adjacent teeth, said splint comprising:

two parallel opposing shoulders an arch portion extending between and connecting the upper ends of the said shoulders two or more prongs extending outwardly from each of said shoulders.

* * * * *